United States Patent [19]

Giesen et al.

[11] Patent Number: 5,578,560
[45] Date of Patent: Nov. 26, 1996

[54] WATER-CONTAINING DETERGENT MIXTURES COMPRISING OLIGOGLYCOSIDE SURFACTANTS

[75] Inventors: Brigitte Giesen; Guenter Kreienfeld; Andreas Syldath, all of Duesseldorf; Karl-Heinz Schmid, Mettmann, all of Germany

[73] Assignee: Henkel Corporation, Plymouth Meeting, Pa.

[21] Appl. No.: 416,814

[22] PCT Filed: Oct. 6, 1993

[86] PCT No.: PCT/EP93/02727

§ 371 Date: Apr. 13, 1995

§ 102(e) Date: Apr. 13, 1995

[87] PCT Pub. No.: WO94/09102

PCT Pub. Date: Apr. 28, 1994

[30] Foreign Application Priority Data

Oct. 14, 1992 [DE] Germany .......................... 42 34 487.5

[51] Int. Cl.$^6$ .............................. C11D 1/72; C11D 1/831
[52] U.S. Cl. .......................... 510/237; 510/405; 510/536
[58] Field of Search .................................. 252/552, 550, 252/554, 173, 174.12, DIG. 14, 135, 531, 174.17

[56] References Cited

U.S. PATENT DOCUMENTS 4,668,422  5/1987  Malik et al. ..................... 252/174.17
5,258,142  11/1993 Geisen et al. ..................... 252/552

FOREIGN PATENT DOCUMENTS

| 0070076 | 1/1983  | European Pat. Off. . |
| 0070075 | 1/1983  | European Pat. Off. . |
| 0070077 | 1/1983  | European Pat. Off. . |
| 0070074 | 1/1983  | European Pat. Off. . |
| 0232153 | 8/1987  | European Pat. Off. . |
| 0301298 | 2/1989  | European Pat. Off. . |
| 0341071 | 11/1989 | European Pat. Off. . |
| 3534082 | 4/1987  | Germany . |
| 9003977 | 4/1990  | WIPO . |
| 9105764 | 5/1991  | WIPO . |
| 9111506 | 8/1991  | WIPO . |

OTHER PUBLICATIONS

Tenside Surf. Det. 28, 413 (1991) No month available.
J. Am. Oil. Chem. Soc. 68, 629 (1991) No month available.

*Primary Examiner*—Erin M. Harriman
*Assistant Examiner*—Necholus Ogden
*Attorney, Agent, or Firm*—Ernest G. Szoke; Wayne C. Jaeschke; Real J. Grandmaison

[57] ABSTRACT

An aqueous detergent composition containing: (a) from 12 to 15% by weight of a nonionic surfactant selected from the group consisting of alkyl oligoglycosides, alkenyl oligoglycosides, and mixtures thereof; (b) from 20 to 30% by weight of an alkyl sulfate; (c) from 40 to 60% by weight of an alkyl ether sulfate; and (d) from 12 to 15% by weight of a component selected from the group consisting of amphoteric surfactants, zwitterionic surfactants, and mixtures thereof, all weights being based on the solids content of the composition.

20 Claims, No Drawings

WATER-CONTAINING DETERGENT MIXTURES COMPRISING OLIGOGLYCOSIDE SURFACTANTS

BACKGROUND OF THE INVENTION

1. Field of the Invention

This invention relates to water-containing detergent mixtures comprising alkyl and/or alkenyl oligoglycosides, alkyl sulfates, alkyl ether sulfates and amphoteric or zwitterionic surfactants, to manual dishwashing detergents containing these mixtures and to the use of the mixtures for the production of surface-active preparations.

2. Discussion of Related Art

Alkyl oligoglycosides and, in particular, alkyl oligoglucosides are nonionic surfactants which, by virtue of their native raw material base (fatty alcohol and sugar), are acquiring increasing significance and are used, for example, in manual dishwashing detergents or cosmetic products [cf. Tens. Surf. Det. 28, 413 (1991)]. However, despite good performance results, there is still a need for detergent mixtures based on alkyl glucosides of which the performance level synergistically exceeds that of the individual components.

There has hitherto been no shortage of attempts to develop detergent mixtures based on alkyl oligoglucosides which have advantageous properties.

EP-B-0 070 074, EP-B-0 070 075, EP-B-0 070 076 and EP-B-0 070 077 (Procter & Gamble), for example, describe high-foaming combinations of alkyl oligoglucosides with anionic surfactants, such as soaps, alkylbenzene sulfonates, fatty alcohol sulfates, conventional fatty alcohol ether sulfates, α-olefin sulfonates and alkane sulfonates and, optionally, betaine surfactants.

DE-A1 35 34 082 describes skin-friendly dishwashing detergents containing a combination of anionic sulfate or sulfonate surfactants, alkyl oligoglucosides and fatty acid alkanolamides.

However, where these known detergent mixtures are used in surface-active preparations, reductions in performance and ecotoxicological compatibility have hitherto had to be accepted in some cases.

Accordingly, the problem addressed by the present invention was to develop detergent mixtures based on alkyl and/or alkenyl oligoglycosides having further improved properties.

DESCRIPTION OF THE INVENTION

The present invention relates to water-containing detergent mixtures comprising—based on the solids content—
a) 5 to 20% by weight of alkyl and/or alkenyl oligoglycosides,
b) 25 to 40% by weight of alkyl sulfates,
c) 35 to 65% by weight of alkyl ether sulfates and
d) 5 to 20% by weight of amphoteric or zwitterionic surfactants.

It has surprisingly been found that the detergent mixtures according to the invention have a washing, dishwashing, foaming and cleaning power and a skin-cosmetic compatibility which exceed those of the individual components through synergistic enhancement.

a) Alkyl and/or alkenyl oligoglycosides (APG) are known substances which may be obtained by the relevant methods of preparative organic chemistry. EP-A1-0 301 298 and WO 90/3977 are cited as representative of the extensive literature available on the subject.

The alkyl and/or alkenyl oligoglycosides correspond to formula (I)

$$R^1\text{—O—}[G]_p \quad (I)$$

in which $R^1$ is a linear or branched alkyl or alkenyl radical containing 4 to 22 carbon atoms, [G] is a glycose unit containing 5 or 6 carbon atoms and p is a number of 1 to 10.

The alkyl and/or alkenyl oligoglycosides may be derived from aldoses or ketoses containing 5 or 6 carbon atoms, preferably from glucose. Accordingly, the preferred alkyl and/or alkenyl oligoglycosides are alkyl and/or alkenyl oligoglucosides.

The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization below 1.7 and, more particularly, between 1.2 and 1.4 are preferred from the performance point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and technical mixtures thereof such as are obtained, for example, in the hydrogenation of technical fatty acid ethyl esters or in the hydrogenation of aldehydes from Roelen's oxo synthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight $C_{12}$ alcohol as an impurity, and alkyl oligoglucosides based on technical $C_{9/11}$ oxoalcohols (DP=1 to 3) are preferred.

The alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof which may be obtained as described above. Alkyl oligoglucosides based on hydrogenated $C_{12/14}$ coconut oil alcohol having a DP of 1 to 3 are preferred.

b) Fatty alcohol sulfates (FAS) which may be used in accordance with the invention correspond to formula (II)

$$R^3\text{O—SO}_3X \quad (II)$$

in which $R^3$ is a linear or branched alkyl or alkenyl radical containing 6 to 22 carbon atoms and X is an alkali metal or alkaline earth metal.

These substances are also known chemical compounds which may be obtained by sulfation of fatty alcohols. Typical examples are the sulfates of caproic alcohol, caprylic alcohol, capric alcohol, lauryl alcohol, myristyl alcohol, cetyl alcohol, palmitoleyl alcohol, stearyl alcohol, oleyl alcohol, elaidyl alcohol, petroselinyl alcohol, arachyl alcohol, gadoleyl alcohol, behenyl alcohol and erucyl alcohol and technical mixtures thereof. Sulfates of technical $C_{12/18}$ coconut oil fatty alcohol or $C_{16/18}$ tallow fatty alcohol cuts in the form of their sodium salts are preferably used.

c) Fatty alcohol ether sulfates (FES), which may be used in accordance with the invention, correspond to formula (III)

$$R^3O\text{---}(CH_2CH_2O)_n\text{---}SO_3X \qquad (III)$$

in which $R^3$ is a linear or branched alkyl or alkenyl radical containing 6 to 22 carbon atoms, n is a number of 1 to 10 and X is an alkali metal or alkaline earth metal.

These substances are also known chemical compounds which may obtained by sulfation of fatty alcohol polyglycol ethers. It is preferred to use FES of the NRE type (NRE=narrow range ethoxylates) which are described, for example, in International patent application WO 91/05 764 and in the synoptic Article by D. L. Smith in J. Am. Oil. Chem. Soc. 68, 629 (1991).

Typical examples are the sulfation products of adducts of 1 to 10 moles of ethylene oxide (normal-range or narrow-range) with 1 mole of caproic alcohol, caprylic alcohol, capric alcohol, lauryl alcohol, myristyl alcohol, cetyl alcohol, palmitoleyl alcohol, stearyl alcohol, oleyl alcohol, elaidyl alcohol, petroselinyl alcohol, arachyl alcohol, gadoleyl alcohol, behenyl alcohol and erucyl alcohol and also technical mixtures thereof. Sulfates of adducts of 2 to 7 moles of ethylene oxide with saturated coconut oil fatty alcohols containing 12 to 18 carbon atoms in the form of their sodium, potassium and/or magnesium salts are preferred. It is preferable to use fatty alcohol ether sulfates derived from corresponding fatty alcohol polyglycol ethers which, in turn, have been produced in the presence of calcined or, more particularly, hydrophobicized hydrotalcite and which therefore have a particularly advantageous narrow homolog distribution.

d) Suitable amphoteric or zwitterionic surfactants are, for example, alkyl betaines, alkyl amidobetaines, aminopropionates, aminoglycinates, imidazolinium betaines and/or sulfobetaines.

Typical examples are the reaction products of primary or tertiary fatty amines, fatty acid amides, fatty acid aminoamines or fatty alkyl imidazolines with sodium chloroacetate, acrylates or chlorohydroxypropane sulfonic acid. Information on the production and structure of the compounds mentioned can be found in Falbe (ed.), "Surfactants in Consumer Products", Springer-Verlag, 1986, pages 114–119. Alkylamidobetaines obtained by condensation of technical $C_{12/14}$ or $C_{12/18}$ coconut oil fatty acid with dimethylaminopropyl amine and subsequent reaction with sodium chloroacetate are preferred.

Water-containing detergent mixtures distinguished by particularly advantageous performance properties comprise—based on the solids content a) 12 to 15% by weight of alkyl and/or alkenyl oligoglycosides,
b) 20 to 30% by weight of alkyl sulfates,
c) 40 to 60% by weight of alkyl ether sulfates and
d) 12 to 15% by weight of amphoteric or zwitterionic surfactants.

In addition, the following components have proved to be particularly advantageous (within the predetermined limits):
fatty alcohol sulfates and fatty alcohol ether sulfates in a ratio by weight of 66:34,
the alkyl and/or alkenyl oligoglycosides and the amphoteric or zwitterionic surfactants in a ratio by weight of 50:50 and the fatty alcohol sulfates/fatty alcohol ether sulfates on the one hand and the alkyl and/or alkenyl oligoglycosides/amphoteric or zwitterionic surfactants on the other hand in a ratio by weight of 70:30.

In gauging the ratio by weight of fatty alcohol sulfate to fatty alcohol ether sulfate, it is important to take into account the fact that FES still generally contain fractions of corresponding FAS.

The water-containing detergent mixtures may be produced by simple mechanical mixing of aqueous solutions of the components, optionally at elevated temperatures of 30° to 50° C.; no chemical reaction takes place during the mixing process. The solids content of the water-containing detergent mixtures may be between 15 and 50% by weight and is preferably between 20 and 40% by weight.

The present invention also relates to manual dishwashing detergents containing—based on the solids content a) 5 to 20% by weight of alkyl and/or alkenyl oligoglycosides,
b) 25 to 40% by weight of alkyl sulfates,
c) 35 to 65% by weight of alkyl ether sulfates and
d) 5 to 20% by weight of amphoteric or zwitterionic surfactants.

In addition to the detergent mixtures mentioned, the water-based manual dishwashing detergents according to the invention may contain other typical constituents, for example other anionic, nonionic or amphoteric or zwitterionic co-surfactants, foam boosters, fragrances, etc. A typical formulation may contain, for example, 47% by weight of FES, 23% by weight of FAS, 15% by weight of APG and 15% by weight of alkylamidobetaine, based on the solids content of the detergent. The solids content of the manual dishwashing detergents may be from 15 to 50% by weight and is preferably from 20 to 40% by weight.

Industrial Applications

The detergent mixtures according to the invention are distinguished by excellent washing, dishwashing and cleaning performance and by advantageous skin-cosmetic and ecotoxicological compatibility.

Accordingly, the present invention also relates to their use in the production of laundry detergents, dishwashing detergents and cleaning preparations, hair-care and personal hygiene preparations, in which they may be present in quantities of 1 to 50% by weight and preferably in quantities of 10 to 30% by weight, based on the preparation.

The following Examples are intended to illustrate the invention without limiting it in any way.

EXAMPLES

I. Surfactants Used

APG: $C_{12/14}$ coconut oil alkyl oligoglucoside Plantaren® APG 600 (30% by weight aqueous paste)
FAS: $C_{12/14}$ coconut oil fatty alcohol sulfate Texapon® LS 35 (35% by weight aqueous paste)
FES: $C_{12/14}$ coconut oil fatty alcohol 2EO adduct sulfate Na salt Texapon® NSO (28% by weight aqueous solution)
AMP: Betaine surfactant based on $C_{12/14}$ coconut oil fatty acid amide Dehyton® K All the surfactants used are products of Henkel KGaA, Düsseldorf, Federal Republic of Germany.

II. Evaluation of Dishwashing Performance (DWP)

Dishwashing performance was determined by the saucer test [Fette, Seifen, Anstrichmitt., 74, 163 (1972)]. To this end, saucers 14 cm in diameter were each soiled with 2 cm$^3$ beef tallow (acid value 9-10) and stored for 24 h at room temperature. The saucers were then rinsed at 50° C. with 5 liters of tap water having a hardness of 16° d. The test mixture was used in a dosage of 0.15 g of active substance/1. The dishwashing test was terminated when the foam had completely disappeared. The results of the dishwashing tests, expressed as the number of clean saucers, are set out in Table 1:

TABLE 1

| | Performance tests Percentages in % by weight | | | | |
|---|---|---|---|---|---|
| Ex. | APG % | FAS % | FES % | AMP % | DWP % |
| 1 | 5 | 30 | 60 | 5 | 13.5 |
| 2 | 10 | 27 | 53 | 10 | 15 |
| 3 | 15 | 23 | 47 | 15 | 16 |
| 4 | 20 | 20 | 40 | 20 | 13.5 |
| C1 | 0 | 34 | 66 | 0 | 10.5 |

We claim:

1. An aqueous detergent composition comprising:
   (a) from 12 to 15% by weight of a nonionic surfactant selected from the group consisting of alkyl oligoglycosides, alkenyl oligoglycosides, and mixtures thereof;
   (b) from 20 to 30% by weight of an alkyl sulfate;
   (c) from 40 to 60% by weight of an alkyl ether sulfate, and
   (d) from 12 to 15% by weight of a component selected from the group consisting of amphoteric surfactants, zwitterionic surfactants, and mixtures thereof, all weights being based on the solids content of the composition.

2. The composition of claim 1 wherein said alkyl oligoglycosides and alkenyl oligoglycosides correspond to formula I:

$$R^1\text{—O—}(G)_p \qquad (I)$$

wherein $R^1$ is a linear or branched alkyl or alkenyl radical containing 4 to 22 carbon atoms, (G) is a glycose unit containing 5 or 6 carbon atoms, and p is a number from 1 to 10.

3. The composition of claim 1 wherein said alkyl sulfate corresponds to formula II:

$$R^3\text{O—SO}_3\text{X} \qquad (II)$$

wherein $R^3$ is a linear or branched alkyl or alkenyl radical containing 6 to 22 carbon atoms and X is an alkali metal or alkaline earth metal.

4. The composition of claim 1 wherein said alkyl ether sulfate corresponds to formula III:

$$R^3\text{O—}(CH_2CH_2O)_n\text{—SO}_3\text{X} \qquad (III)$$

wherein $R^3$ is a linear or branched alkyl or alkenyl radical containing 6 to 22 carbon atoms, n is a number from 1 to 10 and X is an alkali metal or alkaline earth metal.

5. The composition of claim 1 wherein said amphoteric and zwitterionic surfactants are selected from the group consisting of alkyl betaines, alkyl amidobetaines, aminopropionates, aminoglycinates, imidazolinium betaines, sulfobetaines, and mixtures thereof.

6. The composition of claim 1 having a solids content of from 15 to 50% by weight.

7. The composition of claim 1 wherein said component (b) and said component (c) are present in said composition in a ratio by weight of 66:34, respectively.

8. The composition of claim 1 wherein said component (a) and said component (d) are present in said composition in a ratio by weight of 50:50, respectively.

9. The composition of claim 1 wherein said components (b)+(c) and said components (a)+(d) are present in said composition in a ratio by weight of 70:30, respectively.

10. The process of claim 8 wherein said alkyl sulfate corresponds to formula II:

$$R^3\text{O—SO}_3\text{X} \qquad (II)$$

wherein $R^3$ is a linear or branched alkyl or alkenyl radical containing 6 to 22 carbon atoms and X is an alkali metal or alkaline earth metal.

11. A process for producing an aqueous detergent composition comprising combining:
    (a) from 12 to 15% by weight of an aqueous nonionic surfactant selected from the group consisting of alkyl oligoglycosides, alkenyl oligoglycosides, and mixtures thereof;
    (b) from 20 to 30% by weight of an aqueous alkyl sulfate;
    (c) from 40 to 60% by weight of an aqueous alkyl ether sulfate, and
    (d) from 12 to 15% by weight of an aqueous component selected from the group consisting of amphoteric surfactants, zwitterionic surfactants, and mixtures thereof, all weights being based on the solids content of the composition.

12. The process of claim 11 wherein said alkyl oligoglycosides and alkenyl oligoglycosides correspond to formula I:

$$R^1\text{—O—}(G)_p \qquad (I)$$

wherein $R^1$ is a linear or branched alkyl or alkenyl radical containing 4 to 22 carbon atoms, (G) is a glycose unit containing 5 or 6 carbon atoms, and p is a number from 1 to 10.

13. The process of claim 8 wherein said alkyl sulfate corresponds to formula II:

$$R^3{}_2\text{O—SO}_3\text{X} \qquad (II)$$

wherein $R^3$ id a linear or branched alkyl or alkenyl radical containing 6 to 22 carbon atoms and X is an alkali metal or alkaline earth metal.

14. The process of claim 11 wherein said alkyl ether sulfate corresponds to formula III:

$$R^3\text{O—}(CH_2CH_2O)_n\text{—SO}_3\text{X} \qquad (III)$$

wherein $R^3$ is a linear or branched alkyl or alkenyl radical containing 6 to 22 carbon atoms, n is a number from 1 to 10 and X is an alkali metal or alkaline earth metal.

15. The process of claim 11 wherein said amphoteric and zwitterionic surfactants are selected from the group consisting of alkyl betaines, alkyl amidobetaines, aminopropionates, aminoglycinates, imidazolinium betaines, sulfobetaines, and mixtures thereof.

16. The process of claim 11 wherein said composition has a solids content of from 15 to 50% by weight.

17. The process of claim 11 wherein said component (b) and said component (c) are present in said composition in a ratio by weight of 66:34, respectively.

18. The process of claim 11 wherein said component (a) and said component (d) are present in said composition in a ratio by weight of 50:50, respectively.

19. The process of claim 11 wherein said components (b)+(c) and said components (a)+(d) are present in said composition in a ratio by weight of 70:30, respectively.

20. The process of claim 11 wherein said composition contains an auxilliary component selected from the group consisting of anionic co-surfactants, nonionic co-surfactants, amphoteric co-surfactants, zwitterionic co-surfactants, foam boosters, fragrances, and mixtures thereof.

* * * * *